(12) United States Patent
Mantzilas et al.

(10) Patent No.: US 9,061,996 B2
(45) Date of Patent: Jun. 23, 2015

(54) SOLID PHASE EXTRACTION METHOD

(75) Inventors: Dimitrios Mantzilas, Oslo (NO); Gry Helene Olaussen, Oslo (NO); Torild Wickstrom, Oslo (NO); Eric Horn, Amersham (GB); Imtiaz Khan, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 13/993,108

(22) PCT Filed: Dec. 14, 2011

(86) PCT No.: PCT/EP2011/072781
§ 371 (c)(1),
(2), (4) Date: Jun. 11, 2013

(87) PCT Pub. No.: WO2012/080349
PCT Pub. Date: Jun. 21, 2012

(65) Prior Publication Data
US 2013/0261315 A1  Oct. 3, 2013

Related U.S. Application Data

(60) Provisional application No. 61/423,114, filed on Dec. 15, 2010.

(30) Foreign Application Priority Data

Dec. 15, 2010  (GB) .................................. 1021263.7

(51) Int. Cl.
*C07D 209/84* (2006.01)
*G01N 21/00* (2006.01)
*C07D 209/82* (2006.01)
*C07B 59/00* (2006.01)

(52) U.S. Cl.
CPC ............ *C07D 209/84* (2013.01); *C07B 59/002* (2013.01)

(58) Field of Classification Search
CPC ........................... C07D 209/82; C07D 209/84
USPC .......................................... 422/554; 548/448
See application file for complete search history.

(56) References Cited

FOREIGN PATENT DOCUMENTS

WO   2007/109007   9/2010

OTHER PUBLICATIONS

PCT/EP2011/072781 ISRWO Dated Mar. 27, 2012.
GB1021263.7 Search Report Dated March 25, 2011.

*Primary Examiner* — Samantha Shterengarts
(74) *Attorney, Agent, or Firm* — Parks Wood LLC

(57) ABSTRACT

The present invention provides a method to prepare an $^{18}$F-labelled tricyclic indole compound comprising a solid-phase extraction (SPE) purification step. This method is particularly suitable for carrying out the radiofluorination method on an automated synthesizer. In addition to the radiofluorination method, the present invention provides a cassette designed to carry out the method on an automated synthesizer.

23 Claims, 1 Drawing Sheet

| Approx. initial activity (MBq) | UEOS(%) (not corr. For RCP(%)) | RAC, MBq/ml | RCP, % RCP-T0 | Hydroxy impurity µg/ml | Compound 1a µg/ml | Acetyl impurity µg/ml | Compound 1 µg/ml | Other impurities µg/ml | Sum µg/ml |
|---|---|---|---|---|---|---|---|---|---|
| 45364 | 23 | 381 | 97.8 | 0.63 | 1.67 | 0.08 | 0.04 | 0.56 | 2.98 |
| 40600 | 40 | 408 | 98.2 | 1.52 | 0.72 | 0.20 | 0.04 | 0.36 | 2.84 |
| 42800 | 37 | 434 | 97.3 | 1.39 | 0.89 | 0.18 | 0.07 | 0.28 | 2.79 |
| 89400 | 44 | 1012 | 96.3 | 0.63 | 0.08 | 0.15 | 0.13 | 0.36 | 1.36 |
| 97100 | 48 | 1170 | 95.1 | 0.54 | 0.07 | 0.17 | 0.16 | 0.29 | 1.23 |
| 114200 | 51 | 1423 | 95.7 | 0.76 | 0.10 | 0.20 | 0.18 | 0.43 | 1.67 |
| 45400 | 43 | 539 | 97.6 | 0.61 | 0.07 | 0.15 | 0.06 | 0.13 | 1.02 |
| 40300 | 56 | 601 | 97.9 | 0.56 | 0.06 | 0.09 | 0.17 | 0.25 | 1.13 |
| 42301 | 42 | 652 | 98.3 | 0.40 | 0.06 | 0.09 | 0.27 | 0.49 | 1.30 |
| 45176 | 41 | 685 | 97.6 | 0.36 | 0.06 | 0.09 | 0.09 | 0.56 | 1.17 |
| 72162 | 39 | 1026 | 97.2 | 0.63 | 0.06 | 0.12 | 0.05 | 0.69 | 1.55 |
| 40700 | 46 | 504 | 97.7 | 0.50 | 0.04 | 0.07 | 0.13 | 0.34 | 1.07 |
| 176 | 49 | 3 | NA | 0.72 | 0.11 | 0.28 | 0.04 | 0.22 | 1.35 |
| 137 | 52 | 2 | NA | 0.59 | 0.06 | 0.19 | 0.04 | 0.11 | 0.99 |
| 37380 | 17 | 232 | 98.5 | 0.03 | 0.02 | 0.03 | 0.04 | 0.41 | 0.52 |
| 142 | 46 | 2 | NA | 0.18 | 0.02 | 0.14 | 0.04 | 0.15 | 0.53 |
| 40800 | 11 | 120 | 98.8 | 0.01 | 0.01 | 0.01 | 0.01 | 0.49 | 0.54 |
| 40400 | 24 | 262 | 98.4 | 0.04 | 0.01 | 0.04 | 0.10 | 0.20 | 0.39 |
| 44000 | 25 | 227 | 98.9 | 0.05 | 0.01 | 0.04 | 0.02 | 0.43 | 0.55 |

SOLID PHASE EXTRACTION METHOD

This application is a filing under 35 U.S.C. 371 of international application number PCT/EP2011/072781, filed Dec. 14, 2011, which claims priority to Great Britain application number 1021263.7 filed Dec. 15, 2010 and to U.S. application No. 61/423,114 filed Dec. 15, 2010, the entire disclosure of which is hereby incorporated by reference.

TECHNICAL FIELD OF THE INVENTION

The present invention relates to radiochemistry and in particular to a method for the preparation of a radiofluorinated compound. The method of the invention provides a radiofluorination method that comprises purification by solid-phase extraction (SPE).

DESCRIPTION OF RELATED ART

Radioflourinated tricyclic indole compounds are known from WO 2010/109007. These compounds are useful as in vivo imaging agents that bind with high affinity to peripheral benzodiazepine receptors (PBR). The compounds also have good uptake into the brain following administration and good selective binding to PBR.

Abnormal PBR expression is known to be a feature of a variety of disease states, and in particular disease states comprising neuroinflammation. The PBR selective ligand, (R)-[$^{11}$C]PK11195 provides a generic indicator of central nervous system (CNS) inflammation. However, (R)-[$^{11}$C] PK11195 is known to have high protein binding, and low specific to non-specific binding. Furthermore, the role of its radiolabelled metabolites is not known, and quantification of binding requires complex modelling. A radiofluorinated tricyclic indole compound of the type disclosed by WO 2010/109007 is therefore poised to provide an improved PBR selective in vivo imaging agent useful in the diagnosis and monitoring of a variety of disease states.

In the experimental examples of WO 2010/109007 the preparation of radiolabelled tricyclic indole compounds is described and includes purification of the compounds using high-performance liquid chromatography (HPLC). HPLC requires a column, high pressure pumps, and an ultraviolet detector which is a relatively complex system.

[$^{18}$F]-radiotracers in particular are now often conveniently prepared by means of an automated radiosynthesis apparatus, e.g. Tracerlab™ and FASTlab™ from GE Healthcare Ltd. For synthesisers like FASTlab™, a single-use disposable cassette in which the radiochemistry is performed is fitted to the apparatus. The cassette normally includes fluid pathways, a reaction vessel, and ports for receiving reagent vials and ideally solid phase extraction (SPE) cartridges for post-radiosynthetic clean up steps. WO 2010/109007 discloses that a preferred method to obtain the radiolabelled tricyclic indole compounds taught therein is by use of an automated synthesiser, wherein purification is preferably carried out by solid phase extraction (SPE). However, no particular methods are described.

It would be desirable to have an optimised method for the production of $^{18}$F-labelled tricyclic indole compounds wherein all the steps including purification are designed to be carried out by means of an automated synthesiser.

SUMMARY OF THE INVENTION

The present invention provides a method to prepare an $^{18}$F-labelled tricyclic indole compound wherein purification is carried out by solid-phase extraction (SPE) rather than HPLC. This method is particularly suitable for carrying out the radiofluorination method on a cassette suitable for use with an automated synthesiser. In addition to the radiofluorination method, the present invention provides a cassette designed to carry out the method on an automated synthesiser.

DETAILED DESCRIPTION OF THE INVENTION

In one embodiment the present invention relates to a method to obtain a radiofluorinated compound of Formula I:

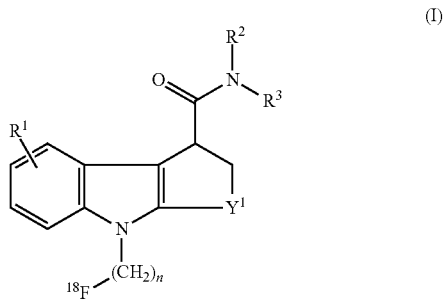

wherein:
R$^1$ is hydrogen, halo or C$_{1-3}$ alkoxy;
R$^2$ and R$^3$ are independently methyl, ethyl or benzyl, or together with the nitrogen to which they are attached form a pyrrolidinyl, piperidinyl, azepanyl, or morpholinyl ring;
Y$^1$ is CH$_2$, CH$_2$—CH$_2$, CH(CH$_3$)—CH$_2$, or CH$_2$—CH$_2$—CH$_2$; and;
n is 1, 2 or 3.
wherein said method comprises:
(i) providing a precursor compound of Formula Ia:

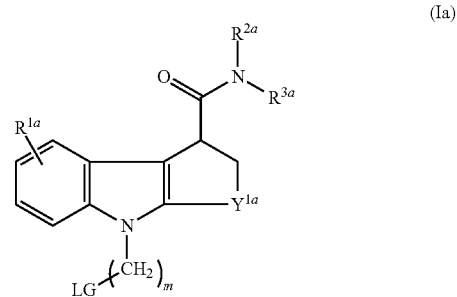

wherein R$^{1a-3a}$, Y$^{1a}$ and m are as defined for and are each the same as R$^{1-3}$, Y$^1$ and n of Formula I, respectively, and LG is a sulfonate leaving group having the formula —O—SO$_2$—R$^{4a}$ wherein R$^{4a}$ is a halogen, a straight-chain or branched-chain C$_{1-10}$ alkyl, a straight-chain or branched-chain C$_{1-10}$ haloalkyl, and a C$_{6-10}$ aryl;
(ii) reacting said precursor compound of Formula Ia with a suitable source of [$^{18}$F]-fluoride;
(iii) purifying the reaction mixture obtained in step (ii), wherein said purifying step comprises:
(a) providing one or more solid-phase extraction (SPE) cartridges wherein the sorbent comprises particles having a diameter between 10-120 µm and bonded hydrocarbons;

(b) conditioning said one or more SPE cartridges;
(c) loading the reaction mixture onto said one or more conditioned SPE cartridges;
(d) washing said one or more SPE cartridges onto which said mixture is loaded using a first solvent system comprising a ratio of water:water-miscible organic solvent in the range 100:0-0:100; and,
(e) eluting said one or more SPE cartridges following said washing step using a second solvent system comprising a ratio of water:water-miscible organic solvent in the range 70:30-0:100.

The term "halogen" or "halo-" means a substituent selected from fluorine, chlorine, bromine or iodine.

Unless otherwise specified, the term "alkoxy" means an alkyl radical comprising an ether linkage. The term "alkyl" means a straight-chain or branched-chain radical having the general formula $C_xH_{2x+1}$, e.g. methyl, ethyl, and propyl. The term "ether linkage" refers to the group —C—O—C—. Examples of suitable alkyloxy radicals include methoxy, ethoxy, ethoxyethyl, and propoxy.

The term "methyl" refers to the alkyl radical of formula $C_xH_{2x+1}$ as defined above wherein x is 1.

The term "ethyl" refers to the alkyl radical of formula $C_xH_{2x+1}$ as defined above wherein x is 2.

The term "benzyl" refers to the monovalent aromatic radical $C_6H_5CH_2$—.

An "aromatic" radical is a conjugated hydrocarbon group with a number of π electrons that equals (4z+2), wherein z is a positive integer or zero (Huckel's rule). The rule applies to hydrocarbons compounds composed of only $sp^2$-hybridized carbon atoms.

The term "pyrrolidinyl" refers to a five-membered aliphatic heterocycle containing four carbon atoms and one nitrogen atom having the molecular formula $C_4H_8N$.

An "aliphatic" radical is either acyclic or cyclic and is not aromatic.

The term "piperidinyl" refers to a six-membered aliphatic heterocycle containing five carbon atoms and one nitrogen atom having the molecular formula $C_5H_{10}N$.

The term "azepanyl" refers to a seven-membered aliphatic heterocycle containing five carbon atoms and one nitrogen atom having the molecular formula $C_6H_{12}N$.

The term "morpholinyl" refers to a six-membered aliphatic heterocycle containing four carbon atoms, one nitrogen atom and one oxygen atom having the molecular formula $C_4H_8NO$.

A "precursor compound" comprises a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity.

The term "leaving group" generally refers to a moiety suitable for nucleophilic substitution and is a molecular fragment that departs with a pair of electrons in heterolytic bond cleavage. In the present invention, reaction of the precursor compound with [$^{18}$F]-fluoride results in the nucleophilic displacement of the sulfonate leaving group from the precursor compound.

The term "[$^{18}$F]-fluoride" refers to the anion $^{18}F^-$.

The term "solid-phase extraction" (SPE) refers to the chemical separation technique that uses the affinity of solutes dissolved or suspended in a liquid (known as the mobile phase) for a solid through which the sample is passed (known as the stationary phase or sorbent) to separate a mixture into desired and undesired components. The result is that either the desired analytes of interest or undesired impurities in the sample are retained on the sorbent.

The portion that passes through the sorbent is collected or discarded, depending on whether it contains the desired analytes or undesired impurities. If the portion retained on the sorbent includes the desired analytes, they can then be removed from the sorbent for collection in an additional step, in which the sorbent is rinsed with an appropriate eluent. The sorbent is typically packed between two porous media layers within an elongate cartridge body to form a "solid-phase extraction (SPE) cartridge" wherein one or more SPE cartridges may be included in a cassette suitable for use with an automated synthesiser. A typical SPE cartridge comprises a syringe barrel made from medical-grade plastic such as polypropylene that is fitted with a luer tip, with frits holding the sorbent within the syringe barrel.

The "sorbent" comprises particles, typically silica-based, to which have been bonded a specific functional group. In the case of the present invention the sorbent suitably comprises particles having a diameter between 10-120 μm. The functional groups bonded to the sorbent particles are hydrocarbon chains of variable length. Typical hydrocarbon chain lengths for SPE cartridge sorbents are C2, C8, C18 and C30.

The term "conditioning" refers to the step of rinsing the SPE sorbent with solvent prior to loading the sample (in this case the reaction mixture). For the present invention, the conditioning step typically comprises application of a water-miscible organic solvent followed by water or an aqueous buffer.

The term "reaction mixture" refers to the crude product of the reaction between the precursor compound of Formula Ia and the suitable source of [$^{18}$F]-fluoride. For example, the reaction mixture is not subjected to any other purification steps such as HPLC prior to loading onto the one or more conditioned SPE cartridges. The purifying step is therefore the entire purification process for the reaction mixture.

The term "loading" as it applies to loading the reaction mixture onto the conditioned SPE cartridges simply refers to the application of the reaction mixture to the cartridge, or in the case of more than one cartridge to the first in the series.

The term "purifying" means the process of separating a desired chemical compound from a mixture that comprises the desired chemical compound along with unwanted chemical compounds. In the context of the present invention the term purifying specifically refers to SPE purifying wherein SPE is as defined above; HPLC is specifically excluded. The aim of purifying is to remove as much as possible of the unwanted chemical compounds and as little as possible of the desired chemical compound so that the desired chemical compound is obtained in as high a proportion of the chemical composition of the purified product as possible. In the specific context of the present invention, the purified product should suitably have a ratio of compounds of Formula Ia:Formula I in the range 20:80 to 0:100. In reality a ratio of 0:100 may not be achievable, therefore ratios of around 10:90 to 1:99 are aimed for, with ratios in the range 5:95 to 1:99 being preferred. Most preferably, other impurities are removed in addition to precursor compound of Formula Ia. As the radiofluorinated compound of Formula I is intended for in vivo use as a positron-emission tomography (PET) tracer, it is necessary to remove any impurities that may have a toxic effect on the mammalian body. Also, in order for the radiofluorinated compound of Formula I to bind most effectively to its biological target, it is desirable to remove as much as possible of any impurities that have binding affinity to the same biological target. The purifying step should result in the retention of as much radiofluorinated compound of Formula I as possible; suitably ≥75%, preferably ≥90%, and most preferably ≥95%.

The term "washing" refers to the step of the SPE procedure tailored for the removal of unwanted impurities from the reaction mixture, i.e. in the case of the present invention any chemical compounds in the reaction mixture other than the radiofluorinated compound of Formula I. In particular, it is desired to remove any unreacted compound of Formula Ia.

The term "solvent system" refers either to a single aliquot of solvent of a particular concentration, or to multiple aliquots of solvent having different concentrations. Suitably, said first solvent system comprises multiple aliquots of solvent wherein the concentration of water-miscible organic solvent decreases with each successive aliquot. Suitably, said second solvent system comprises one or more aliquots wherein the concentration of water-miscible solvent is greater than that of any of the aliquots used in the first solvent system. The volume of an aliquot in the context of the present invention can suitably be between 1-50 mL, typically between 5-30 mL.

The term "water-miscible organic solvent" refers to a solvent other than water that readily forms a homogenous solution with water at room temperature and at atmospheric pressure. Examples of suitable water-miscible organic solvents include ethanol, methanol, isopropanol, acetonitrile, dimethylformamide, dimethyl sulfoxide and formic acid. For example, the solvent system could comprise one or more aliquots of 35% aqueous ethanol as well as one or more aliquots of 40% aqueous ethanol and one or more aliquots of 55% aqueous ethanol.

The term "eluting" refers to the step of the SPE procedure designed to remove the compound of interest (the radiofluorinated compound of Formula I) from the SPE cartridge, but to leave behind any impurities not removed by the washing step.

$R^1$ of Formula I is preferably $C_{1-3}$ alkoxy and is most preferably methoxy.

$R^2$ and $R^3$ of Formula I are preferably both methyl or both ethyl, and most preferably both ethyl.

$Y^1$ of Formula I is preferably $CH_2$—$CH_2$.

In Formula I n is preferably 2.

$R^{1a}$ of Formula Ia is preferably $C_{1-3}$ alkoxy and is most preferably is methoxy.

$R^{2a}$ and $R^{3a}$ of Formula Ia are preferably both methyl or both ethyl, and most preferably both ethyl.

$Y^{1a}$ of Formula Ia is preferably $CH_2$—$CH_2$.

In Formula Ia, m is preferably 2.

LG of Formula Ia is preferably selected from toluenesulfonic acid (tosylate), nitrobenzenesulfonic acid, benzenesulfonic acid, trifluoromethanesulfonic acid (triflate), fluorosulfonic acid, methanesulfonic acid (mesylate) and perfluoroalkylsulfonic acid. In a most preferred embodiment LG is tosylate, triflate or mesylate and is especially preferably mesylate.

In an especially preferred radiofluorinated compound of Formula I:
  $R^1$ is $C_{1-3}$ alkoxy and preferably is methoxy;
  $R^2$ and $R^3$ are either both methyl or both ethyl, and preferably both ethyl;
  $Y^1$ is $CH_2$—$CH_2$; and
  n is 2.

In an especially preferred precursor compound of Formula Ia:
  $R^{1a}$ is $C_{1-3}$ alkoxy and preferably is methoxy;
  $R^{2a}$ and $R^{3a}$ are either both methyl or both ethyl, and preferably both ethyl;
  $Y^{1a}$ is $CH_2$—$CH_2$;
  m is 2; and, LG is selected from toluenesulfonic acid (tosylate), nitrobenzenesulfonic acid, benzenesulfonic acid, trifluoromethanesulfonic acid (triflate), fluorosulfonic acid, methanesulfonic acid (mesylate) and perfluoroalkylsulfonic acid; preferably tosylate, triflate or mesylate and most preferably mesylate.

Said radiofluorinated compound of Formula I is preferably Compound 1:

and said precursor compound of Formula Ia is preferably Compound 1a:

wherein OMs is mesylate.

The compounds of Formula I and Formula Ia have a chiral centre and been illustrated above as their racemates. In a particularly preferred embodiment, the compounds of Formula I and Formula Ia are provided in an enantiomerically pure form, preferably the S-enantiomer. The S-enantiomer of Compound I is as follows:

and the S-enantiomer of Compound Ia is as follows:

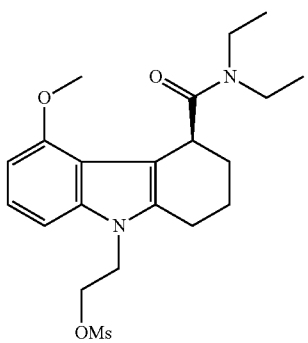 [SMILES: CCN(CC)C(=O)[C@H]1CCCc2c1c1c(OC)cccc1n2CCOS(C)(=O)=O]

A preferred particle diameter distribution for the sorbent of said one or more SPE cartridges is between 35-120 µm, more preferably between 35-60 µm and most especially preferably between 35-55 µm. Preferably, within this size distribution, the sorbent of the one or more SPE cartridges includes at least some particles having a diameter of between 35-40 µm, with more preferred sorbents comprising a greater proportion of particles having a diameter between 35-40 µm. Furthermore, it is preferred that the bonded hydrocarbons of said sorbent have a chain length of C18 or C30. It is also preferred that said one or more SPE cartridges used in step (iii) of the purifying step comprise between 300 mg and 3.0 g of sorbent, and most preferably between 1.5-2.0 g of sorbent. The amount of sorbent can generally be provided as 1-3 SPE cartridges, typically two SPE cartridges. For example, in a particularly preferred embodiment, 2 SPE cartridges having 900 mg of sorbent each are provided. Non-limiting examples of commercially-available SPE cartridges that are suitable for use in the purifying step of the method of the invention include e.g. Waters tC18 Sep Pak Plus 900 mg, Waters C18 Sep Pak Plus 360 mg, Varian Bond Elute 500 mg, Macherey Nagel C18 ec 530 mg, Princeton C30 950 mg. Preferred of these commercially-available SPE cartridges are the Waters tC18 Sep Pak Plus 900 mg, Varian Bond Elute 500 mg and Princeton C30 950 mg, with the Waters tC 18 Sep Pak Plus 900 mg being most preferred.

The preferred embodiments of the SPE cartridges as described in the previous paragraph are particularly preferred where the method of the invention relates to obtaining Compound 1 by radiofluorination of Compound 1a.

Preferably, in the purifying step of the method of the invention, said water-miscible organic solvent of said first and second water-miscible organic solvent systems is selected from ethanol (EtOH), acetonitrile (MeCN), methanol and isopropanol. Preferably, the first solvent system comprises one or more aliquots having water:water-miscible organic solvent in a ratio of between 65:35-60:40, i.e. 35-40% aqueous water-miscible organic solvent, wherein each successive aliquot used in the first solvent system has a lower concentration of water-miscible organic solvent, e.g. a first aliquot of 40% aqueous water-miscible organic solvent followed by a second aliquot of 35% aqueous water-miscible organic solvent. Preferably, the volume of said first aliquot is greater than that of said second aliquot, e.g. said first aliquot is 20-30 mL and said second aliquot is 5-15 mL. Preferably, said second solvent system comprises one or more aliquots of aqueous water-miscible organic solvent each having water:water-miscible organic solvent in a ratio of between 60:40 to 0:100, i.e. 40-100% aqueous water-miscible organic solvent. Most preferably, said second solvent system comprises one or more aliquots wherein the concentration of water-miscible organic solvent is greater than that of any of the aliquots in the first solvent system. For example, said second solvent system preferably comprises one or more aliquots having a concentration of water-miscible organic solvent in the range 50-80%, most preferably 50-70% and most especially preferably 50-60%. Said first and second solvent systems may also comprise an aliquot of water as a final aliquot. The most preferred water-miscible organic solvent for said first and second water-miscible organic solvent systems is EtOH. Most preferably when EtOH is said water-miscible organic solvent, in said first solvent system a first aliquot is 40% aqueous water-miscible organic solvent and a second aliquot is 35% aqueous water-miscible organic solvent, optionally followed by a third aliquot of water; and, in said second solvent system a first aliquot is 50-60% aqueous EtOH, optionally followed by subsequent aliquots having EtOH concentration greater than said first aliquot.

Non-limiting examples of particularly preferred solvent systems for use in the purifying step of the method of the invention are tabulated below (% values are % water-miscible organic solvent in water, where said organic solvent is preferably EtOH):

| Solvent System | Aliquot # | | |
|---|---|---|---|
| First | 1 | 27 mL 40% | 22 mL 40% |
| | 2 | 10 mL 35% | 10 mL 35% |
| | 3 | 5 mL H$_2$O | — |
| Second | 1 | 3 mL 50% | 3.5 mL 55% |
| | 2 | 3 mL 65% | 3.5 mL H$_2$O |
| | 3 | 3 mL 100% | — |

The preferred embodiments described in the above paragraph relating to solvent systems are particularly preferred where the method of the invention relates to obtaining Compound 1 by radiofluorination of Compound 1a, and in particular the S-enantiomers thereof.

The method of the invention primarily aims to remove as much unreacted precursor compound of Formula Ia from the reaction mixture as possible. In preferred embodiments, the method of the invention also removes additional impurities. Notably, where the method of the invention relates to obtaining Compound 1 by radiofluorination of Compound 1a, the experimental examples demonstrated that the method of the invention removes 90-98% of the precursor compound and 85-90% of a hydroxy impurity and only traces of a vinyl impurity are left. The hydroxy and vinyl impurities are, respectively, as follows:

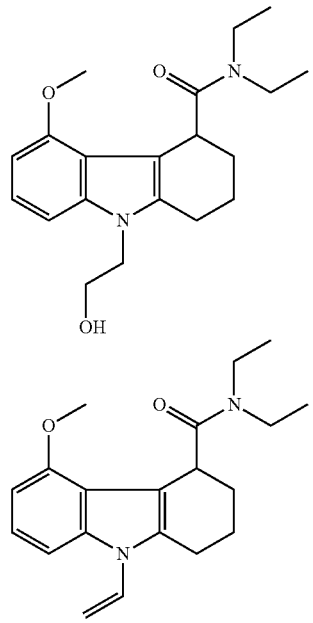

A further notable impurity is the acetyl impurity, which has the following structure:

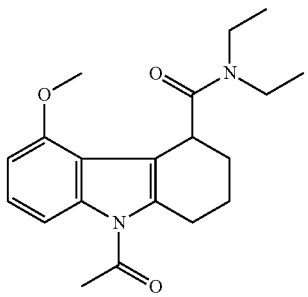 [SMILES: CCN(CC)C(=O)C1CCCc2c1c1c(OC)cccc1n2C(C)=O]

Methods suitable for the preparation of precursor compound of Formula Ia are described in detail in WO 2010/109007. For example, a precursor compound wherein LG is mesylate can be prepared from commercially-available starting materials according to the general method illustrated in Scheme 1 below:

Scheme 1

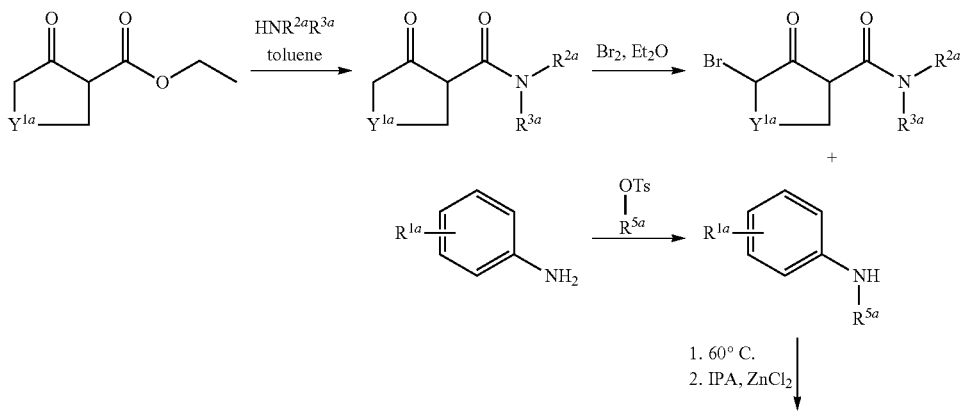

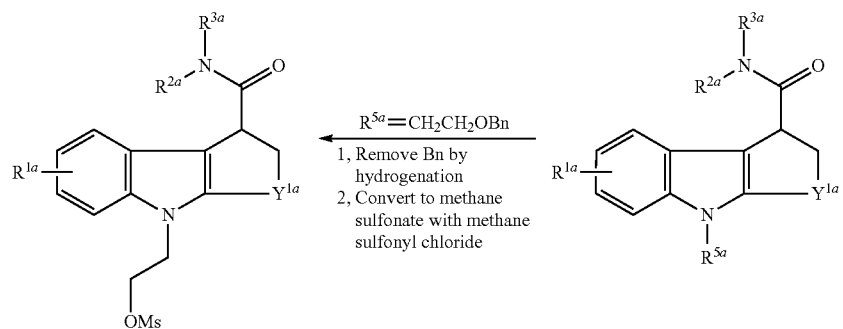

In Scheme 1 above and in Scheme 1a below, the variables $R^{1a-3a}$ and $Y^{1a}$ are as suitably and preferably provided herein in respect of Formula Ia. $R^{5a}$ in Scheme 1 represents $CH_2CwaterBn$ wherein Bn is benzyl, Et is ethyl, OTs represents a tosylate leaving group, IPA stands for isopropyl alcohol, and OMs represents a mesylate leaving group.

Alternatively, where $R^{1a}$ of the precursor compound of Formula Ia is at the top position on the ring, the general synthetic route illustrated in Scheme Ia below can be used:

resulting from the presence of water, water is typically removed from [$^{18}$F]-fluoride prior to the reaction, and fluorination reactions are carried out using anhydrous reaction solvents (Aigbirhio et at 1995 J Fluor Chem; 70: 279-87). The removal of water from [$^{18}$F]-fluoride is referred to as making "naked" [$^{18}$F]-fluoride. A further step that is used to improve the reactivity of [$^{18}$F]-fluoride for radiofluorination reactions is to add a cationic counterion prior to the removal of water. Suitably, the counterion should possess sufficient solubility

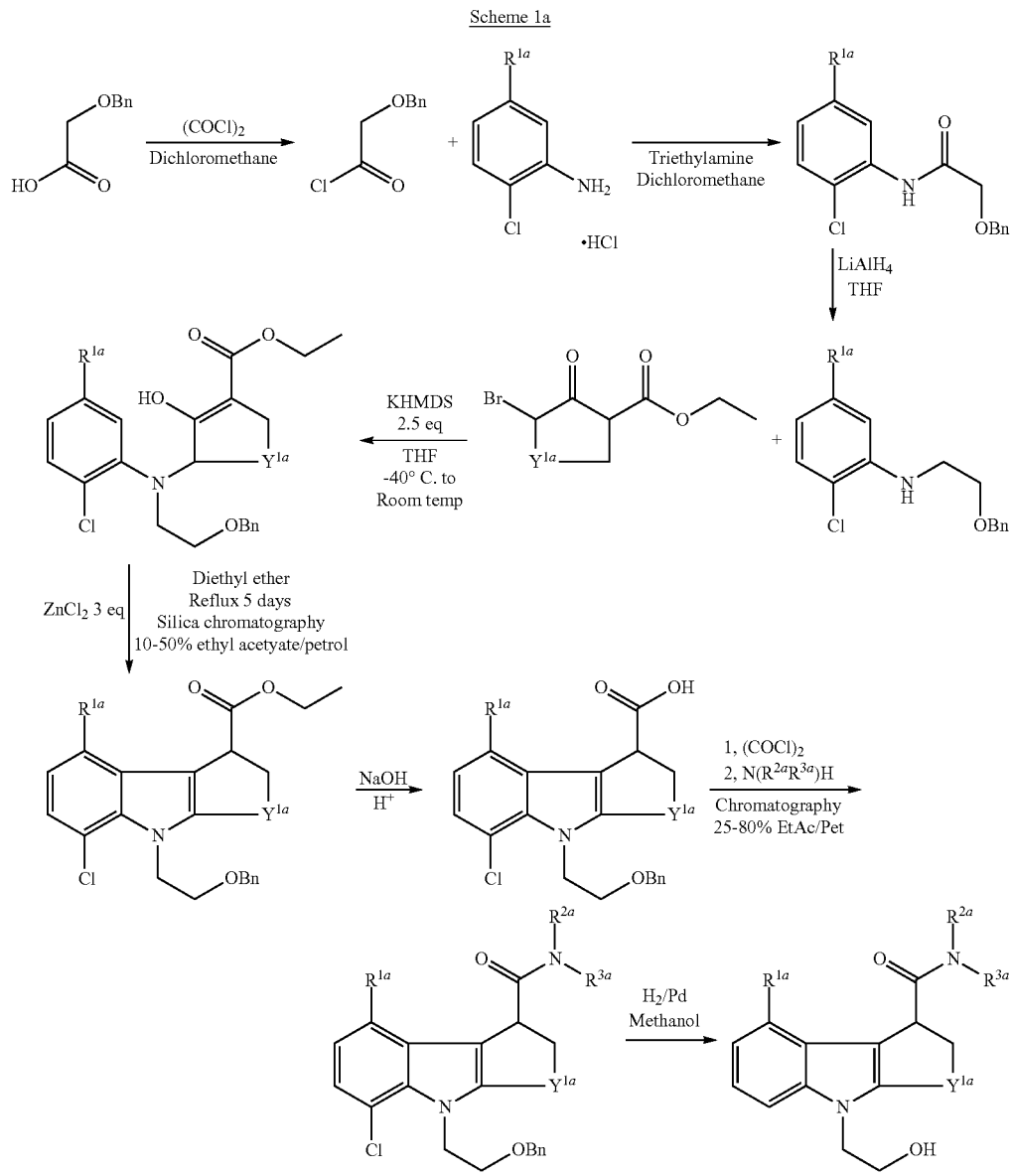

Scheme 1a

In Scheme 1a, Bn is benzyl, THF is tetrahydrofuran, KHMDS is potassium hexamethyldisilazane, eq stands for equivalent(s), and EtAc is ethyl acetate. The resultant hydroxyl compound can be readily converted into a precursor compound of Formula Ia, e.g. by reaction with methane sulfonyl chloride for addition of a methane sulfonate leaving group.

[$^{18}$F]-fluoride is normally obtained as an aqueous solution from the nuclear reaction $^{18}O(p,n)^{18}F$. In order to increase the reactivity of fluoride and to avoid hydroxylated by-products within the anhydrous reaction solvent to maintain the solubility of the [$^{18}$F]-fluoride. Therefore, counterions that are typically used include large but soft metal ions such as rubidium or caesium, potassium complexed with a cryptand such as Kryptofix™, or tetraalkylammonium salts, wherein potassium complexed with a cryptand such as Kryptofix™, or tetraalkylammonium salts are preferred. [$^{18}$F]-fluoride that has been made reactive according to these steps is what is meant in the context of the present invention as a "suitable source of [$^{18}$F]-fluoride".

[¹⁸F]-radiotracers in particular are now often conveniently prepared on an automated radiosynthesis apparatus. There are several commercially-available examples of such apparatus, including Tracerlab™ and FASTlab™ (GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. In a preferred embodiment therefore, the method of the invention is automated.

Additionally, in a further aspect, the present invention provides a cassette for carrying out the method of the invention on an automated synthesis apparatus, wherein said cassette comprises:
 (i) a vessel containing a precursor compound of Formula Ia as defined herein for the method of the invention;
 (ii) means for eluting the vessel with a suitable source of [¹⁸F]-fluoride; and,
 (iii) one or more SPE cartridges as defined herein for the method of the invention.

All the suitable, preferred, most preferred, especially preferred and most especially preferred embodiments of the precursor compound of Formula Ia, [¹⁸F]-fluoride and the SPE cartridges that are presented herein in respect of the method of the invention also apply to the cassette of the invention.

The cassette of the invention may furthermore comprise:
 (iv) an ion-exchange cartridge for removal of excess [¹⁸F]-fluoride.

The invention is now illustrated by the following non-limiting examples:

BRIEF DESCRIPTION OF THE EXAMPLES

Example 1 describes the preparation of spiked samples for SPE screening experiments.
Example 2 describes the SPE screening experiments.
Example 3 describes preparation of decayed FASTLab crude samples for SPE purification experiments.
Example 4 describes the SPE purification of Crude 1.
Example 5 describes the SPE purification of Crude 2.
Example 6 describes the SPE purification of Crude 3.
Example 7 describes the SPE purification of Crudes 4 & 5.
Example 8 describes the SPE purification of Crude 6.
Example 9 describes a number of FASTlab runs that were carried out including SPE purification on the FASTlab cassette.

LIST OF ABBREVIATIONS USED IN THE EXAMPLES aq aqueous
DAD diode array detector
ESI electrospray ionisation
EtOH ethanol
HPLC high performance liquid chromatography
LC-MS liquid chromatography mass spectrometry
MeCN acetonitrile
MS mass spectrometry
SPE solid phase extraction
UV ultraviolet

EXAMPLES

Example 1

Preparation of Spiked Samples for SPE Screening Experiments

Non-radioactive Compound 1 and Compound 1a were prepared in accordance with the methods described in Examples 2 and 1, respectively, of WO 2010/109007.

To prepare each spiked sample, 1 mg of Compound 1a was weighed in and dissolved in 1 mL of MeCN. Then 100 µl of Compound 1 stock solution (1 mg/mL in 50:50 $H_2O$:MeCN) was added. The sample was then diluted with 1 mL of water before use in the experiments described in Example 2 below.

Example 2

SPE Screening Experiments

Samples containing ~25 µg of Compound 1 (a compound of Formula I) and 1 mg of Compound 1a (a compound of Formula Ia) were prepared.

2 mL of sample in 50% aq MeCN was used in each experiment. Before application of sample, the cartridge(s) were activated using 3 mL EtOH, equilibrated using 10 mL water, and dried by application of a vacuum. Following the washing steps, the cartridge(s) were dried by application of a vacuum, then eluted using 3 mL EtOH and dried again by application of a vacuum.

Analysis of the various fractions was carried out by HPLC with an Agilent 1100 Series, OSLC016 with UV detection at 230 nm, 270 nm, DAD detection and MS detection. The column used was a Zorbax Stable Bond C18 1.8 µm 4.6×50 mm and the mobile phases were A: 0.1% HCOOH in water, B: 0.1% HCOOH in 80% MeCN. The flow rate was 1 mL/min and the column oven was set to 40° C. The following gradient was used:

| Time | % B |
|---|---|
| 0 | 40 |
| 0.30 | 40 |
| 5.50 | 70 |
| 6.30 | 90 |
| 9.20 | 90 |
| 9.30 | 40 |
| 12.00 | 40 |

Amounts of Compound 1 and Compound 1a were estimated based on standard curves generated for Compound 1.

Analysis was also carried out by LC-MS using an Agilent single TOF (LC-UV/MS) in ESI+ ionization mode and a fragmentor voltage of 70V. Detection was carried out by UV at 230 nm, 270 nm, DAD detection and MS detection. The column was a Zorbax Stable Bond C18 1.8 µm 4.6×50 mm and the mobile phases were A: 0.1% HCOOH in water, B: 0.1% HCOOH in 80% MeCN. The flow rate was 1.5 mL/min and the column oven was set to 40° C. The following gradient was used:

| Time | % B |
|---|---|
| 0 | 40 |
| 0.30 | 40 |
| 5.50 | 70 |

-continued

| Time | % B |
|---|---|
| 6.30 | 90 |
| 9.20 | 90 |
| 9.30 | 40 |
| 12.00 | 40 |

The table below summarises the experiments carried out and the results obtained:

| Cartridge(s) | Washes | Precursor:Product | % Recovery of Product |
|---|---|---|---|
| 2 × tC18-Sep Pak Plus, 900 mg (Waters) | 27 mL 40%, 10 mL 35% aq EtOH, 5 mL H₂O, 3 mL 50% aq EtOH | 1:99 | 95 |
| 1 × Bond Elute, 500 mg (Varian) | 4 × 5 mL 40% aq EtOH 3 × 5 mL 35% aq EtOH | 6:94 | 93 |
| 2 × C18 ec, 530 mg (Macherey-Nagel) | 6 × 5 mL 40% aq EtOH | 1:99 | 75 |
| 2 × C30, 950 mg (Princeton) | 30 mL 40% aq EtOH 20 mL 35% aq EtOH | 17:83 | 97 |

Example 3

Preparation of FASTLab Crude Samples for SPE Purification Experiments

Generally for the preparation of each FASTLab crude sample, a FASTLab cassette was assembled with an eluent vial, a QMA cartridge (preconditioned, Waters), a precursor vial and an MeCN vial. The FASTLab samples were prepared by carrying out the FASTLab process up to and including the labelling step, followed by transfer of the crude (approximately 1.3 mL MeCN) to a vial for storage in until analysis. For the non-radioactive runs, the labelling step was carried out without any fluoride. More detail in respect of each sample is now provided.

Crude 1

120.6 MBq of [$^{18}$F]fluoride obtained from a GE PETrace cyclotron was made up to 1.5 mL with water, introduced into the FASTLab synthesiser (GE Healthcare), and trapped on the QMA cartridge. 825 μL eluent solution (KHCO$_3$+kryptofix in MeCN/water (80/20, v/v)) was used to elute the [$^{18}$F] fluoride off the QMA cartridge into the reaction vessel. The material in the reaction vessel was then dried at 120° C. for 10 minutes followed by transfer of 4.0 mg of Compound 1a dissolved in 1.6 mL MeCN to the reaction vessel. Labelling was carried out at 100° C. for 15 minutes. The contents of the reaction vessel following labelling (in 1.3 mL MeCN) were transferred to a vial and allowed to decay at room temperature for 1 day prior to storage in the freezer until analysis.

500 μL decayed crude in 500 μL MeCN was spiked with 40 μL 1.1 mg/mL Compound 1 and then diluted with 1 mL water; 2 mL of this was used in the experiment described in Example 4.

Crudes 2 & 3

The process as described for Crude 1 was carried out except that (i) instead of trapping $^{18}$F-fluoride on the QMA cartridge, 1.5 mL water was passed through the QMA cartridge, (ii) 1200 μL of eluent solution was used rather than 825 μL eluent solution, (iii) drying was at 100° C. for 20 minutes, and (iv) 3.2 mg of Compound 1a in 1.6 mL MeCN was transferred to the reaction vessel for the labelling reaction step.

Samples were prepared for 2 experiments. For each sample, 500 μL crude (in MeCN) was spiked with 20 μL Compound 1 solution (1.24 mg/mL in 50:50 H$_2$O:MeCN) and then diluted with 1 mL water. 2 mL of each solution was loaded onto the SPE column for the experiments described in Examples 5 and 6.

Crude 4

The process as described for the preparation of Crudes 2 and 3 was carried out except that 3.1 mg of Compound 1a in 1.6 mL MeCN was used for the labelling reaction step.

500 μL crude (in MeCN) was spiked with 20 μL Compound 1 solution (1.24 mg/mL in 50:50 H$_2$O:MeCN) and then diluted with 1 mL water. 2 mL of this solution was loaded onto the SPE column for the experiment described in Example 7.

Crude 5

The process as described for the preparation of Crudes 2 and 3 was carried out except that 4.8 mg of Compound 1a in 1.6 mL MeCN was used for the labelling reaction step.

500 μL crude (in MeCN) was spiked with 20 μL Compound 1 solution (1.24 mg/mL in 50:50 H$_2$O:MeCN) and then diluted with 1 mL water. 2 mL of this solution was loaded onto the SPE column for the experiment described in Example 7.

Crude 6

The process as described for the preparation of Crudes 2 and 3 was carried out except that 3.5 mg of Compound 1a in 1.6 mL MeCN was used for the labelling reaction step.

500 μL crude (in MeCN) was spiked with 20 μL Compound 1 solution (1.24 mg/mL in 50:50 H$_2$O:MeCN) and then diluted with 1 mL water. 2 mL of this solution was loaded onto the SPE column for the experiment described in Example 8.

The table below details the amounts in μg of the main components in the FASTLab crude samples prepared according to this example as applied to the SPE cartridges in Examples 4-8:

| Crude # | Hydroxy | Compound 1a | Compound 1 | Vinyl |
|---|---|---|---|---|
| 1 (before spiking) | 32.0 | 500.0 | 0.8 | 39.0 |
| 2 | 47.0 | 354.0 | 21.0 | 50.0 |
| 3 | 45.0 | 347.0 | 20.0 | 49.0 |
| 4 | 151.0 | 877.0 | 22.0 | 123.0 |
| 5 | 186.0 | 1648 | 23.0 | 188 |
| 6 | 89.0 | 1397 | 1.4 | 102.2 |

Example 4

SPE Purification of Crude 1

2×900 mg Waters tC18 SPE cartridges were used in series. The cartridges were activated with 3 mL EtOH, equilibrated with 10 mL water and dried by application of a vacuum. Then, 2 mL Crude 1 (prepared as described in Example 3) was applied to the cartridges. The cartridges were washed firstly with 27 mL 40% aq EtOH, then 10 mL 35% aq EtOH, and then 5 mL water. The cartridges were then dried by application of a vacuum, followed by elution using 3 mL EtOH and a further drying step.

Analysis of the various fractions was carried out by HPLC as described in Example 2 above.

The table below details the amounts of each component in μg coming off the cartridges following each step:

| Wash | Hydroxy | Compound 1a | Compound 1 | Vinyl |
|---|---|---|---|---|
| 27 mL 40% aq EtOH | 26 | 777 | 0 | 0 |
| 5 mL 35% aq EtOH | 17 | 147 | 0 | 0 |
| 2.5 mL 35% aq EtOH | 7 | 24 | 0 | 0 |
| 2.5 mL 35% aq EtOH | 7 | 12 | 0 | 0 |
| 5 mL water | 3 | 4 | 0 | 0 |
| 3 mL EtOH | 31 | 7 | 60 | 96 |

Approximately 80% of Compound 1a and 30% of the hydroxy are removed during the wash with 27 mL 40% aq EtOH. Another 20% of Compound 1a and 30% of the hydroxy are removed during the wash with 35% EtOH (total of 10 mL). Only small amounts of Compound 1a and hydroxy are removed during the wash with 5 mL water. Left in the eluate is hydroxy/Compound 1a/Compound 1/vinyl to a ratio 18/3/36/43. As expected, no vinyl is removed as it elutes later than Compound 1.

Example 5

SPE Purification of Crude 2

The method as described in Example 4 was used for 2 mL of Crude 2 (prepared as described in Example 3) except that elution was carried out using 3 mL of 50% aq EtOH, 3 mL of 60% aq EtOH, 3 mL 70% aq EtOH and 3 mL of 80% aq EtOH were used.

The table below details the amounts of each component in μg coming off the cartridges following each step:

| Wash | Hydroxy | Compound 1a | Compound 1 | Vinyl |
|---|---|---|---|---|
| 27 mL 40% aq EtOH | 5 | 261 | 0 | 0 |
| 10 mL 35% aq EtOH | 15 | 74 | 0 | 0 |
| 5 mL water | 1 | 2 | 0 | 0 |
| 3 mL 50% aq EtOH | 14 | 2 | 1 | 0 |
| 3 mL 60% aq EtOH | 4 | 1 | 22 | 0 |
| 3 mL 70% aq EtOH | 0 | 1 | 0 | 41 |
| 3 mL 80% aq EtOH | 0 | 1 | 0 | 6 |

Compound 1 eluted mainly during the 3 mL of 60% aq EtOH, but some Compound 1 was also observed in the 3 mL of 50% aq EtOH and 3 mL 70% aq EtOH. 85% of the vinyl eluted during the 3 mL of 70% aq EtOH and the last 15% during 3 mL of the 80% aq EtOH. The wash with 50% aq EtOH before elution and after the wash with 5 mL water was shown to be effective for the removal of the hydroxy.

Example 6

SPE Purification of Crude 3

The method as described in Example 5 was used to purify 2 mL of Crude 3 (prepared as described in Example 3) except that the 3 mL 50% aq EtOH step was changed to a 3 mL 40% aq EtOH step, and followed by 3 mL of 65% aq EtOH and 3 mL of 100% EtOH.

The table below details the amounts of each component in μg coming off the cartridges following each step:

| Wash | Hydroxy | Compound 1a | Compound 1 | Vinyl |
|---|---|---|---|---|
| 27 mL 40% aq EtOH | 5 | 261 | 0 | 0 |
| 10 mL 35% aq EtOH | 15 | 74 | 0 | 0 |
| 5 mL water | 1 | 2 | 0 | 0 |
| 3 mL 40% aq EtOH | 14 | 2 | 1 | 0 |
| 3 mL 65% aq EtOH | 4 | 1 | 22 | 0 |
| 3 mL 100% aq EtOH | 0 | 1 | 0 | 41 |

The removal of hydroxy decreases as compared to the method described in Example 5, but less loss of Compound 1 was observed. Compound 1 mainly eluted in the 3 mL of 65% aq EtOH wash.

Example 7

SPE Purification of Crudes 4 & 5

Crudes 4 and 5 were purified using the method as described in Example 4, except that the 3 mL EtOH step was replaced with 3 mL 50% aq EtOH, then 3 mL 65% EtOH, and then 3 mL 100% EtOH, with each of these steps followed by drying by application of a vacuum.

The table below details the amounts of each component in μg coming off the cartridges following each step in respect of Crude 4:

| Wash | Hydroxy | Compound 1a | Compound 1 | Vinyl |
|---|---|---|---|---|
| 27 mL 40% aq EtOH | 16 | 688 | 0 | 0 |
| 10 mL 35% aq EtOH | 58 | 274 | 0 | 0 |
| 5 mL water | 8 | 6 | 0 | 0 |
| 3 mL 50% aq EtOH | 61 | 7 | <1 | 0 |
| 3 mL 65% aq EtOH | 21 | 1 | 25 | <1 |
| 3 mL 100% aq EtOH | 0 | 0 | <1 | 197 |

The table below details the amounts of each component in μg coming off the cartridges following each step in respect of Crude 5:

| Wash | Hydroxy | Compound 1a | Compound 1 | Vinyl |
|---|---|---|---|---|
| 27 mL 40% aq EtOH | 18 | 1054 | 0 | 0 |
| 10 mL 35% aq EtOH | 60 | 450 | 0 | 0 |
| 5 mL water | 8 | 164 | 0 | 0 |
| 3 mL 50% aq EtOH | 62 | 13 | <1 | 0 |
| 3 mL 65% aq EtOH | 22 | <1 | 24 | <1 |
| 3 mL 100% aq EtOH | 0 | 0 | <1 | 155 |

The experiments for Crude 4 and Crude 5 showed similar trends. After the wash with 27 mL of 40% aq EtOH approximately 60-70% of Compound 1a was removed together with approximately 10% of the hydroxy impurity. The 10 mL wash with 35% aq EtOH removed nearly the rest of Compound 1a. A total of 90% was removed for Crude 5 (the total amount Compound 1a in the injected sample was 1.7 mg) and 98% Crude 4 (the total amount of Compound 1a in the injected sample was 0.9 mg). A total of 40-50% of the hydroxy was removed after this wash. 5 mL water washed out further amounts of both hydroxy and Compound 1a. The wash with 3 mL of 50% aq EtOH removed another 35% of the hydroxy and small amounts of Compound 1a. The 3 mL of 65% aq EtOH, contained 50/50 Compound 1/hydroxy and traces of Compound 1a and vinyl. This means that approximately 85-90% of the hydroxy was removed during the procedure. The vinyl impurity is mainly trapped on the cartridge and eluted out with 100% EtOH.

Crude 5 contains almost double μgs of Compound 1a compared to Crude 4, but the results are comparable. The method was able to remove nearly all Compound 1a in both crudes.

Example 8

SPE Purification of Crude 6

An experiment was performed to examine the composition in the eluate when the sample injected was not spiked with product. SPE purification was performed on Crude 6 (prepared as described in Example 3) with the method as described in Example 7 for the purification of Crudes 4 and 5.

The table below details the amounts of each component in μg coming off the cartridges following each step:

| Wash | Hydroxy | Compound 1a | Compound 1 | Vinyl |
|---|---|---|---|---|
| 27 mL 40% aq EtOH | <0.115 | 618.0 | 0 | 0 |
| 10 mL 35% aq EtOH | 17.7 | 421.1 | 0 | 0 |
| 5 mL water | 2.3 | 9.0 | 0 | 0 |
| 3 mL 50% aq EtOH | 34.8 | 21.9 | 0.2 | 0 |
| 3 mL 65% aq EtOH | 16.0 | 1.1 | 0.7 | 0 |
| 3 mL 100% aq EtOH | 0 | 0 | 0 | 82.5 |

The table shows that the composition (based on estimated amounts [μg]) of the eluate is hydroxyl/precursor/product/vinyl=90/6/4/0. The ratio given in the table is based on the area under the peak at 230 nm. The lowest values included in the standard curve were 0.115 μg.

Example 9

FASTlab Runs

A FASTlab process was carried out for the production of a number of batches of the S-enantiomer of Compound 1. Up to 80 GBq of [$^{18}$F]fluoride obtained from a GE PETrace cyclotron (from $H_2^{18}O$) was introduced into the FASTLab synthesiser (GE Healthcare), and trapped on the QMA cartridge. Approximately 475 μl eluent solution ($KHCO_3$+kryptofix in MeCN/water (80/20, v/v) was used to elute the [$^{18}$F]fluoride off the QMA cartridge into the reaction vessel. The material in the reaction vessel was then dried at 120° C. for 9 minutes followed by transfer of 4.0 mg of Compound 1a dissolved in 1.6 mL MeCN to the reaction vessel. Labelling was carried out at 100° C. for 6 minutes.

In each case, following labelling, the reaction mixture was applied to the first in a series of 2 conditioned 900 mg Waters tC18 SPE cartridges in situ on the FASTlab cassette and the SPE purification process was carried out as follows: a first solvent system comprising 22 mL 40% EtOH followed by 10 mL 35% EtOH and a second solvent system comprising 3.5 mL 55% EtOH and 3.5 mL water.

FIG. 1 provides details of the runs that were carried out, including initial activity, uncorrected end of synthesis (UEOS) yield, radioactive concentration (RAC), radiochemical purity (RCP), as well as the amounts of each compound (all S-enantiomer compounds) separated in the SPE process. RCP values in excess of 95% were routinely achieved.

What is claimed is:

1. A method to obtain a radiofluorinated compound of Formula I:

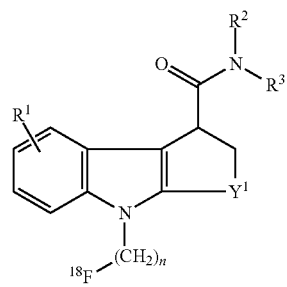

(I)

wherein:
R$^1$ is hydrogen, halo or C$_{1-3}$ alkoxy;
R$^2$ and R$^3$ are independently methyl, ethyl or benzyl, or together with the nitrogen to which they are attached form a pyrrolidinyl, piperidinyl, azepanyl, or morpholinyl ring;
Y$^1$ is CH$_2$, CH$_2$—CH$_2$, CH(CH$_3$)—CH$_2$, or CH$_2$—CH$_2$—CH$_2$; and;
n is 1, 2 or 3;
wherein said method comprises:
(i) providing a precursor compound of Formula Ia:

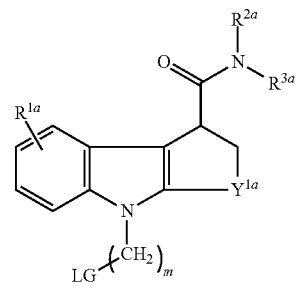

(Ia)

wherein R$^{1a-3a}$, Y$^{1a}$ and m are as defined for and are each the same as R$^{1-3}$, Y$^1$ and n of Formula I, respectively, and LG is a sulfonate leaving group;
(ii) reacting said precursor compound of Formula Ia with a suitable source of [$^{18}$F]-fluoride;
(iii) purifying the reaction mixture obtained in step (ii), wherein said purifying step comprises:
  (a) providing one or more solid-phase extraction (SPE) cartridges wherein the sorbent comprises particles having a diameter between 10-120 μm and bonded hydrocarbons;
  (b) conditioning said one or more SPE cartridges;
  (c) loading the reaction mixture onto said one or more conditioned SPE cartridges;
  (d) washing said one or more SPE cartridges onto which said mixture is loaded using a first solvent system comprising a ratio of water:water-miscible organic solvent in the range 100:0-0:100; and,
  (e) eluting said one or more SPE cartridges following said washing step using a second solvent system comprising a ratio of water:water-miscible organic solvent in the range 70:30-0:100;
with the proviso that in said purifying step HPLC is specifically excluded.

2. The method as defined in claim 1 wherein each of R$^1$ and R$^{1a}$ is C$_{1-3}$ alkoxy.

3. The method as defined in claim 2 wherein each of $R^1$ and $R^{1a}$ is methoxy.

4. The method as defined in claim 1 wherein each of $R^2$, $R^3$, $R^{2a}$ and $R^{3a}$ is either methyl or ethyl.

5. The method as defined in claim 4 wherein each of $R^2$, $R^3$, $R^{2a}$ and $R^{3a}$ is ethyl.

6. The method as defined in claim 1 wherein each of $Y^1$ and $Y^{1a}$ is $CH_2$—$CH_2$.

7. The method as defined in claim 1 wherein each of n and m is 2.

8. The method as defined in claim 1 wherein LG is selected from tosylate, triflate and mesylate.

9. The method as defined in claim 8 wherein LG is mesylate.

10. The method as defined in claim 1 wherein said radiofluorinated compound of Formula I is:

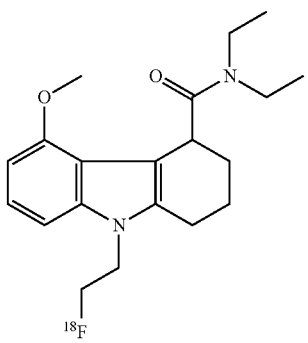 [SMILES: CCN(CC)C(=O)C1CCCc2c1c1c(OC)cccc1n2CC[18F]]

and said precursor compound of Formula Ia is:

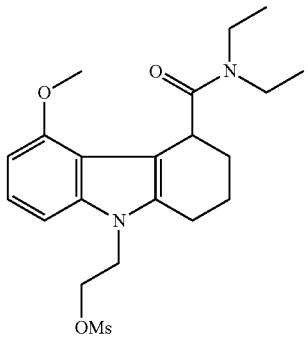 [SMILES: CCN(CC)C(=O)C1CCCc2c1c1c(OC)cccc1n2CCOS(C)(=O)=O]

wherein OMs is mesylate.

11. The method as defined in claim 1 wherein said one or more SPE cartridges used in step (iii) comprise between 900 mg and 2.0 g of sorbent.

12. The method as defined in claim 11 wherein said one or more SPE cartridges comprise between 1.5-2.0 g of sorbent.

13. The method as defined in claim 1 wherein the sorbent of said SPE cartridges used in step (ii) comprises particles having a diameter distribution of between 35-60 μm.

14. The method as defined in claim 1 wherein for said SPE cartridges used in step (ii) said bonded hydrocarbons of said sorbent have a carbon chain length of 18 or 30.

15. The method as defined in claim 1 wherein said water-miscible organic solvent of said first and second water-miscible organic solvent systems used in step (ii) of said method is selected from ethanol (EtOH) and acetonitrile (MeCN).

16. The method as defined in claim 15 wherein said water-miscible organic solvent is EtOH.

17. The method as defined in claim 16 wherein said first solvent system comprises one or more aliquots of aqueous EtOH each having water:EtOH in a ratio of between 65:35-60:40, and one or more aliquots of water.

18. The method as defined in claim 17 wherein said second solvent system comprises one or more aliquots of aqueous EtOH each having water:EtOH in a ratio of between 60:40-0:100.

19. The method as defined in either claim 17 wherein said first solvent system consists of a first aliquot of 27 mL 40% EtOH, a second aliquot of 10 mL 35% EtOH, and a third aliquot of 5 mL water; and wherein said second solvent system consists of a first aliquot of 3 mL 50% EtOH, a second aliquot of 3 mL 65% EtOH and a third aliquot of 3 mL 100% EtOH.

20. The method as defined in either claim 17 wherein said first solvent system consists of a first aliquot of 22 mL 40% EtOH and a second aliquot of 10 mL 35% EtOH; and wherein said second solvent system consists of a first aliquot of 3.5 mL 55% EtOH, a second aliquot of 3.5 mL water.

21. The method as defined in claim 1 which is automated.

22. A cassette for carrying out an automated method of claim 1 which comprises:
(i) a vessel containing a precursor compound of Formula Ia as defined in claim 1;
(ii) means for eluting the vessel with a suitable source of [$^{18}F$]-fluoride; and,
(iii) one or more SPE cartridges as defined in claim 1.

23. The cassette as defined in claim 22 which further comprises:
(iv) an ion-exchange cartridge for removal of excess [$^{18}F$]-fluoride.

* * * * *